United States Patent [19]
Cigaina et al.

[11] Patent Number: 6,041,258
[45] Date of Patent: Mar. 21, 2000

[54] MEDICAL STIMULATION

[75] Inventors: Valerio Cigaina, Treviso, Italy; David Jenkins, Bennington, N.J.

[73] Assignee: Transneuronix, Inc., Mount Arlington, N.J.

[21] Appl. No.: 09/122,832

[22] Filed: Jul. 27, 1998

Related U.S. Application Data

[63] Continuation-in-part of application No. PCT/US98/10402, May 21, 1998.

[51] Int. Cl.⁷ .................................. A61N 1/05; A61N 1/36
[52] U.S. Cl. .................................................. 607/40; 607/41
[58] Field of Search ................................ 607/40, 41, 133

[56] References Cited

U.S. PATENT DOCUMENTS

| | | |
|---|---|---|
| 2,865,376 | 12/1958 | Pellier et al. . |
| 3,760,812 | 9/1973 | Timm et al. . |
| 4,444,207 | 4/1984 | Robicsek . |
| 4,475,560 | 10/1984 | Tarjan et al. . |
| 4,524,771 | 6/1985 | McGregor et al. . |
| 4,901,722 | 2/1990 | Noguchi . |
| 5,059,207 | 10/1991 | Shah . |
| 5,100,431 | 3/1992 | Buster et al. . |
| 5,423,872 | 6/1995 | Cigaina . |
| 5,423,876 | 6/1995 | Camps et al. . |
| 5,433,728 | 7/1995 | Kim . |
| 5,450,739 | 9/1995 | Bogart et al. . |
| 5,489,294 | 2/1996 | McVenes et al. . |
| 5,716,392 | 2/1998 | Bourgeois et al. . |

FOREIGN PATENT DOCUMENTS

| | | |
|---|---|---|
| 44 02 058 | 1/1994 | Germany . |
| WO 97/41921 | 11/1997 | WIPO . |

*Primary Examiner*—William E. Kamm
*Assistant Examiner*—Carl H. Layno
*Attorney, Agent, or Firm*—Fitch, Even, Tabin & Flannery

[57] ABSTRACT

An improved handle for a medical device used in laparoscopic surgery is provided. This handle is especially adapted for use with an implant device specifically for electrostimulation and/or electrical monitoring of endo-abdominal tissue or viscera is provided. The implant device has an elongated body equipped with devices to secure it to the tissue to be treated and two or more electric poles that are electrically connected to an electric connection terminal for connection to a power source, means to penetrate the tissue to be treated, and quick-release connecting devices to separate the penetration device from the elongated body. The handle, which is an elongated body, is attached to the proximal end of the implant device or other medical device and has a grasping means at its opposite end for manipulation with laparoscopic forceps.

14 Claims, 3 Drawing Sheets

MEDICAL STIMULATION

RELATED APPLICATIONS

This application is a continuation-in-part of our International Patent Application Ser. No. PCT/US98/10402, filed on May 21, 1998, which designated the United States as well as other countries and which claimed priority from Italian Application MI97A001246, filed on May 28, 1997.

FIELD OF THE INVENTION

This invention relates to a medical device handle which is designed and adapted for use in laparoscopic surgery. This medical device handle is especially adapted for manipulation by laparoscopic forceps. This medical device handle is also especially adapted for use with an implant device for electrostimulation and/or electrical monitoring of endo-abdominal tissue or viscera, especially an implant device having an elongated body equipped with devices to secure it to the tissue or viscera to be treated and two or more electric poles that are electrically connected to an electric connection terminal for connection to a power source, means to penetrate the tissue or viscera to be treated and quick-release connecting devices to separate the penetration device from the elongated body.

BACKGROUND OF THE INVENTION

It is well known that more than 70% of illnesses affecting the digestive tract are of a functional nature. Today such illnesses are treated predominantly using pharmacological means. Since drugs generally have side effects, particularly when the drugs cure the symptom and not the underlying problem or dsyfunction, they must often be administered temporaly. Indeed, if the side effects are sufficiently serious, the drug may have to be discontinued before full benefit to the patient is realized; in many cases the underlying illness remains.

The important role played by electrophysiology in controlling gastrointestinal activity has become increasingly apparent in recent years. Thus, the possibility exits of correcting dysfunction by means of electrostimulation applied at specific frequencies, sites, and modalities and with regard to the self-regulating electromotor physiology of the gastrointestinal tube. It has recently been shown, for example, that changes occur in the motility and electromotor conduct of the gastric tract in eating disorders (e.g., obesity, thinness, bulimia, anorexia). Disturbances in electromotor activity in diabetic gastroparesis, in reflux in the upper digestive tract, and in numerous other gastroenterological functional pathologies have also been observed.

Stimulation of the intrinsic nervous system of the stomach is likely to have two major consequences or effects: (1) the correction and direct control of the electromotor activity of the intestines and (2) the stimulation of increased incretion of specific substances (i.e., gastroenteric neuromediators) produced by the intrinsic nervous system itself through the myenteric plexus. Curing of functional illnesses involving the digestive system and more broadly involving disorders in any way connected to the digestive system is, therefore, closely linked to the progress of research in the field of electrophysiology.

An indispensable condition for modifying the electrical activity of the digestive system's intestinal tract and the related neurohormonal incretions is the use of an implant system to generate electrical impulses (electrical stimuli) and electric tubes (electrocatheters) to connect them to the viscera and/or intestines to be stimulated. These treatment methods involve a surgical technique to implant the electrocatheter in the abdomen which is known as micro-invasive surgery or video-laparoscopic surgery. Current electrocatheters to stimulate electrically and/or monitor endo-abdominal viscera normally have metal microbarbs which are angled in such a way as to permit application of the end of the catheter and to prevent it from being dislodged. However, this type of catheter is often very complicated to make and consequently is very costly.

Moreover, current electrocatheters are generally very difficult to handle and use. More particularly, surgeons generally find them very difficult to insert because of the many arduous operations required to be performed during the laparoscopic procedure. In such procedures, the patient is first given a general anesthetic, after which his or her abdomen is inflated with $CO_2$ or another inert inflammable gas so as to transform the abdominal cavity from a virtual to a real cavity. Rigid tubes with airtight membranes (i.e., "trocars") are then inserted into the abdominal cavity filled with $CO_2$ so that a video camera and other surgical instruments can be introduced into the abdomen. The operation then proceeds by viewing the video images transmitted by the camera. Normally four or more trocars are used. Generally the first trocar provides access to the abdomen by the video camera in order to monitor the surgical procedure. A service clamp is normally inserted in the second trocar to move or retain the hepatic edge that normally covers the small gastric curve or other viscus depending on the type of operation to be performed. A third trocar provides access for a maneuvering clamp or laparoscopic forceps. The fourth trocar is used for the introduction of the electrocatheter to be implanted in the patient. The structure of the electrocatheter plays an important part in facilitating the specific operation for whichever of the patient's viscera the surgeon aims to stimulate.

Each of the trocars used, of course, requires a separate incision through the skin. To keep the abdomen inflated, valves are used with the trocars, allowing for an airtight seal. Introduction of a medical device, such as an electrocatheter, into the abdomen generally requires the use of laparoscopic forceps to grasp the device. Such devices, which are generally inherently fragile in nature, could be damaged if grasped too firmly by the forceps. Thus, for example in the case of an electrocatheter having electrode leads, the interior conductor wires could be broken, rendering the device useless.

It is, of course, desirable in laparoscopic surgery to limit the number of trocars used since each trocar requires a separate incision which results in additional visible scars for the patent. More importantly, each additional incision increases the chance of infection and other complications resulting therefrom. Therefore, to eliminate an additional trocar, implantable devices are often inserted completely through the trocar and into the abdomen so that the trocar can be used for insertion of other instruments and/or manipulation devices. Thus, the surgeon will often need to pull the distal end of the inserted device back through a trocar and/or remove the device entirely. In this case, the device needs to "line up" to the trocar passageway to be pulled back through the trocar. Of course, if the device is grasped by the forceps in a manner so the longitudinal dimension of the device is not alined with the trocar passageway, the device cannot be pulled back through the trocar.

SUMMARY OF THE INVENTION

This invention relates to a medical device handle which is designed and adapted use in laparoscopic surgery. This medical device handle is especially adapted for manipulation by laparoscopic forceps. This medical device handle is also especially adapted for use with an implant device for electrostimulation and/or electrical monitoring of endo-abdominal tissue or viscera, especially an implant device having an elongated body equipped with devices to secure it to the tissue or viscera to be treated and two or more electric poles that are electrically connected to an electric connection terminal for connection to a power source, means to penetrate the tissue or viscera to be treated and quick-release connecting devices to separate the penetration device from the elongated body. The improved medical device handle can easily be adapted for use with other medical and/or implant devices used in laparoscopic surgery.

An improved implant device for electrostimulation and/or electrical monitoring of the endo-abdominal viscera is also provided. The improved implant device of the present invention is simple to handle and use, especially when used in conjunction with the improved medical device handle described herein, thereby simplifying the surgical procedure required to implant the device. This implant device can be easily inserted and anchored in the viscera to be stimulated without using any type of suture or requiring any maneuvers that might be difficult and risky for the other viscera or for the integrity of the electrocatheter itself. This improved implant device is especially adapted for electrostimulation and/or electrical monitoring of the tissue or viscera of the mammalian body (especially the human body), especially tissue and internal organs the endo-abdominal cavity. Examples of such tissue and internal organs include, but are not limited to, the stomach, intestines, spleen, bladder, muscles, and the like.

It is one object of the present invention to provide a handle for a medical device to be used in laparoscopic surgery. Another object is to provide a handle for a medical device which allows easy insertion into the abdomen and/or removal from the abdomen through a trocar. It is another object of the invention to provide a handle for a medical device which assists in maintaining an airtight seal as the medical device is passed through the trocar. It is still another object of the present invention to provide a handle for a medical device such that grasping with forceps will not damage the underlying device and/or components. Another object of this invention is to provide a grasping and pulling means at the proximal end of the handle so that the handle can easily be grabbed and the medical device can easily be manipulated and/or pulled back through the trocar.

Yet another object of the present invention is to provide a handle for a medical device which allow the handle to be firmly attached to the device but still be easily removed by the surgeon at the appropriate time. When the medical device has electrical connectors at the its proximal end, another object is to allow the handle to serve as a cover or sleeve to prevent fluids from coming in contact with the electrical connections; the surgeon can remove the handle/cover just prior to connecting the device to its electrical power source.

Still another object is to provide a handle for attachment to a laparoscopic medical device having a proximal end and a distal end, said handle comprising (a) an elongated body having a proximal end and a distal end and an essentially circular cross-section suitable for passage through a trocar used in laparoscopic surgery; (b) an attachment means at the distal end of the elongated body whereby the handle can be reversible attached to the proximal end of the laparoscopic medical device; (c) a grasping means at the proximal end of the elongated body whereby the handle can be grasped and manipulated with forceps and thereby pulled, along with any attached laparoscopic medical device, through the trocar; whereby the handle is essentially self-aligning when pulled by forceps through the trocar using the grasping means.

Still another object of the invention is to provide an implant device specifically for electrostimulation and/or electrical monitoring of the endo-abdominal visceral tract that has significant flexibility of use since it is capable of having multiple poles and of being adapted to any surgical requirement without substantially modifying its structure. Another object of the invention is to provide an implant device specifically for electrostimulation and/or electrical monitoring of the endo-abdominal viscera that the surgeon is able to locate easily in order to determine the orientation of its two ends.

Still another object of the invention is to provide an implant device which, once it is anchored in the viscera, is capable of reducing to a minimum its excessive length inside the abdomen. Another object of the invention is to provide an implant device that effectively protects the electrical connection terminal that connects to a power source so as to be able to perform this operation in a dry arena, thereby permitting the entire procedure, including anesthesia, to be carried out in an extremely short time.

A further object of the invention is to provide an implant device specifically for electrostimulation or electrical monitoring of tissue to be treated within the endo-abdominal cavity, said implant device comprising (1) an elongated body having a distal end and a proximal end, (2) a penetration mechanism at the distal end to penetrate the tissue to be treated, (3) a quick release connecting mechanism adjacent to the penetration mechanism, (4) a first and second sets of flexible tines adjacent and proximal to the quick release connecting mechanism to secure the implant device to the tissue to be treated wherein the first and second sets of tines are spaced apart along the elongated body a distance sufficient to span the tissue such that the first set of tines are located between the quick release connecting mechanism and the second set of tines, (5) at least two electric poles located between the two sets of flexible tines, and (6) an electrical connection terminal at the proximal end for connection to a power source wherein the two or more electric poles are electrically connected to electrical connection terminal, and wherein the quick release connecting mechanism is effective to separate the penetration device from the elongated body once the implant device is properly positioned in the endo-abdominal cavity. This implant device is especially useful when used in conjunction with the handle described herein.

These and other features and advantages of the present invention will become apparent to those skilled in the art upon a reading of the following detailed description when taken in conjunction with the drawings wherein there is shown and described preferred embodiments of the invention.

DETAILED DESCRIPTION OF THE PREFERRED EMBODIMENTS

Figure 1:
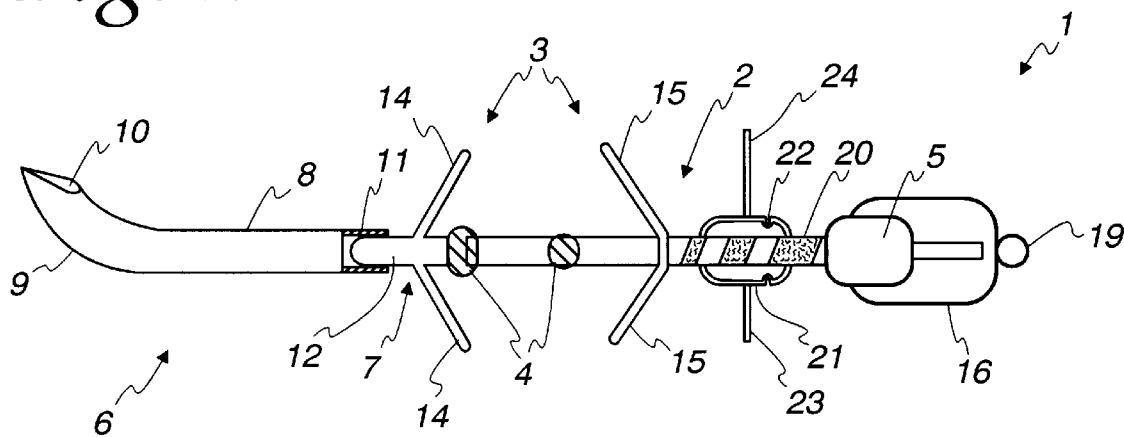
FIG. 1 is a schematic side view of one embodiment of the implant device according to this invention.
Figure 2:
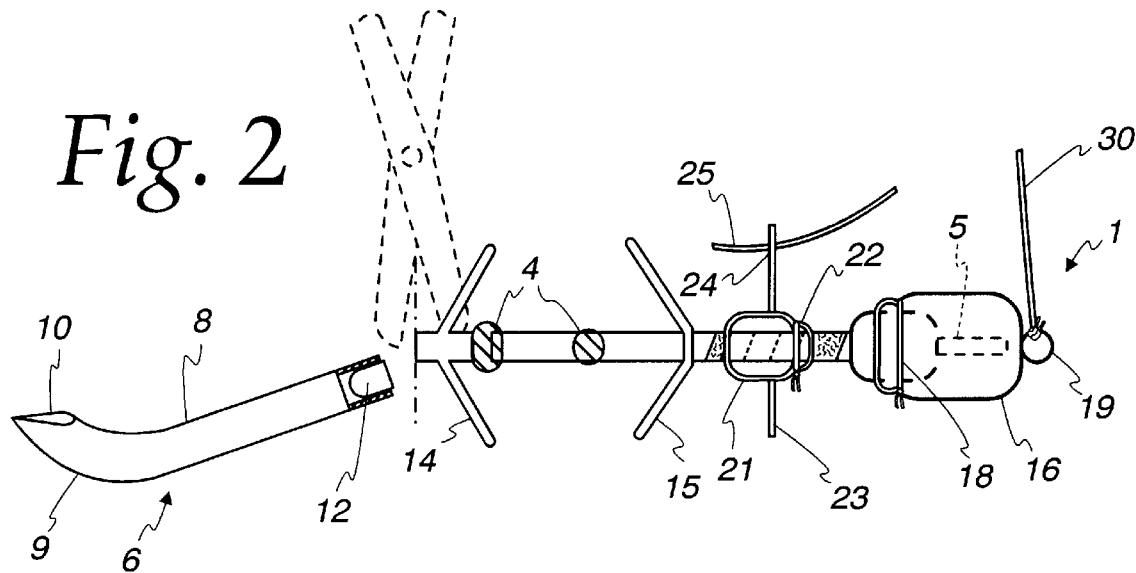
FIG. 2 illustrates how, once the implant device of FIG. 1 has been inserted during the video-laparoscopic operation, the surgeon can easily remove or detach the visceral wall penetrating mechanism that forms part of the implant device according to this invention.

The present invention provides an implant device specifically for electrostimulation and/or electrical monitoring of the endo-abdominal visceral tract. The implant device has an elongated body equipped with devices to secure it to the intestinal wall and two or more electric poles that are electrically connected to an electrical connection terminal for connection to a power source, characterized by the fact that it includes means to penetrate the intestinal wall and a quick release connecting mechanism to separate said penetration device from the elongated body. One embodiment of the present invention is illustrated in FIGS. 1 and 2. The implant device specifically for electrostimulation and/or electrical monitoring of the endo-abdominal viscera is identified overall by reference number 1, and includes an elongated body 2 of the electrocatheter equipped with securing mechanisms 3 (consisting of tines 14 and 15) to secure it to the visceral wall (not shown), and two or more electric poles 4 which are electrically connected to an electrical connection terminal pin 5 that is capable of connecting the electrocatheter to a power source (not shown). The power source may be, for example, an electric pulsator with an operating frequency of a preset number of pulses per minute.

More specifically, and advantageously, the implant device includes penetration mechanism 6 capable of penetrating the intestinal wall and mechanism 7 for connection and quick-release of penetration mechanism 6 to the elongated body 2 of the electrocatheter. In particular, penetration mechanism 6 includes a solid tunneling device or stylet 8 with a smooth, noncutting curved section 9 on the end of which is cutting part 10. Located opposite end 10 is cavity 11 through which the attachment to the elongated body 2 is made. The connection and quick-release mechanism 7 includes a connecting element 12, one end of which is connected to the end of elongated body 2, and the other end of which is connected to the inside of cavity 11 on stylet 8.

The outer insulating cover on elongated body 2 and connecting element 12 are preferably formed from silicone (preferably medical grade) or other biocompatible material having similar stress characteristics. The length of the connecting element 12 is adjusted to permit angling and flexibility without harming the electrical component located within the elongated body. In addition, the connecting element 12 preferably is radiopaque. Advantageously, during video-laparoscopic surgery, in order to separate the stylet 8 from the elongated body 2 of the electrocatheter, it is sufficient to cut it with scissors as shown in FIG. 2 in order to be able to remove the stylet from the abdominal cavity, as will be better explained below.

Furthermore, as can easily be seen from FIGS. 1 and 2, connecting element 12 also has securing parts 3 and in particular first projections, wings, or tines 14 which spread apart, are elastically pliable. Preferably, the securing parts 3 and tines 14 are also made of silicone, but are not radiopaque. Opposite the plurality of first tines 14, the elongated body 2 is equipped with a plurality of second tines 15, which spread apart in the opposite directions from the first tines and are designed to define the deepest point of penetration of the elongated body into the visceral wall. Generally, both the first and second tines are each at least two in number; preferably each set of tines are three to five in number. Preferably, the first tines 14 have a diameter of about 1 mm and a length of about 3 mm and should penetrate the entire thickness of the intestinal wall or other tissue to be stimulated before exiting on the opposite side. As those skilled in the art will realize, both the first and second set of tines may be of different numbers, sizes, and shapes so long as they serve their intended purpose of "locking" the implant to the tissue or viscera to be simulated and/or monitored. The tines are flexible and are preferably formed from silicone (preferably medical grade) or other bio-compatible materials in order to minimize damage or stress to the tissue as the implant device is positioned and, after completion of treatment, removed. Generally the first tines are located about 3–5 mm in front of the first pole 4 of the electrocatheter (the first pole 4 is that pole located nearer the stylet 8). The first pole of the electrocatheter is obviously the beginning of its active electrical conduction with the second pole (also located between the two sets of tines) completing the active electrical connection with the tissue to be stimulated.

In operation, the second tines 15 do not penetrate the thickness of the intestinal wall or other tissue to be stimulated. Rather, they work with the first pair to prevent the electrocatheter from being dislodged after insertion. In effect, the two sets of tines 14 and 15 allow the electrocatheter to be "locked" in place relative to the tissue to be stimulated without the need for any suturing to anchor the electrocatheter, which could damage it. The distance between the first and second pair of tines may be vary as needed, and will depend upon the desired distance between the cathode and the anode (i.e., the first and second poles 4 located between the two sets of tines). Of course, the desired distance between the two poles will be related to the thickness of the tissue intended to be stimulated. The distance between the cathode and the anode can also vary depending upon whether the electrical simulator is used only for stimulation or for electrical monitoring and/or whether an electrocatheter with several poles is to be used. Preferably, the linear part of stylet 8 has a length that is at least equal to the distance between the first and second sets of tines 14 and 15.

The implant device may also include a cover or cap 16 that consists, for instance, of a removable and insulating sheath which has, in addition, sealing element 18. The sheath includes a small covering, also of silicone, which guarantees both the impermeability of connecting terminal 5 for the entire time it is in the abdomen during insertion, and during its recovery for electrical connection. For this reason the sheath includes the sealing element consisting of binding 18 which keeps it watertight, prevents any contact between the biological fluids and electric terminal 5, and prevents the sheath from breaking off by force of the traction to which it is subjected when the electrical connecting terminal is extracted from the abdomen. The sheath is, moreover, equipped with a means to recover the electrocatheter after implanting, which consists of ring 19 which can be attached to thread 30 of a predetermined length. The unattached end of thread 30 remains outside the abdominal cavity and thereby permits recovery of the electric terminal end of the electrocatheter.

If desired, the elongated body may have a series of graphic representations 20, each one of which is different from the other, which can be used to indicate the orientation and location of the electrocatheter during the implant procedure. The purpose of the graphic representations 20 is to indicate to the surgeon the location of the two ends of the electrocatheter during the insertion operation For example, the graphic representations could consist of black zebra stripes that increase in size as they moves toward electric terminal 5. Of course, other graphic representations could be used so long as they allow the orientation and location of the electrocatheter to be determined visually (through the video camera) during the implantation procedure.

In addition, the elongated body shown in FIGS. 1 and 2 has a sliding cylindrical cursor 21 equipped with a seat 22 which permits it to be stopped at a desired position on the elongated body. The cursor has a discoidal extension 23 with one or more small holes 24 through which thread 25 may be inserted, which permits the electrocatheter to be attached to a membrane outside the abdominal cavity. After the electrocatheter is anchored to the viscera (i.e., the tissue to be stimulated and/or monitored), the surgeon can move the small cylinder to the desired position on the electrocatheter and attach it to the outside of the abdominal cavity so as to reduce to a minimum the excessive length of the electrocatheter inside the abdomen itself.

In operation, once the patient has been given a general anesthesia and the appropriate trocars have been inserted, it is possible to maneuver from outside all the instruments that are used by means of a monitor that transmits the images from the video camera. At this point, the surgeon should see to it that sheath 16 is tightly secured by binding 18 to electrical terminal 5. Then the surgeon proceeds to connect thread 30 to ring 19 attached to sheath 16. After the electrocatheter is placed in the abdominal cavity, the surgeon keeps thread 30, which is anchored to said ring and must be of sufficient length, outside the abdomen. By means of the live images from the camera it is easy to identify the back end of the electrocatheter thanks to the zebra stripes 20 on it, and thus, stylet 8 which is secured by a needle holder or clamp is introduced into the thickness of the small gastric curve, taking care not to enter the gastric cavity. For this purpose, a gastroscopy may be performed during the tunneling operation.

When stylet 8 has completed its journey it is gently pushed so as to cause the first pair of tines 14 to exit the tunnel created by stylet. The second pair of tines 15 stops outside the tunnel created by the stylet. In this position, the tissue to be stimulated is located between the two pairs of tines 14 and 15. Moreover, the electrocatheter is effectively "locked" in place by the two pairs of tines 14 and 15. Positioned between the two tines, and therefore inside the transmuscular tunnel, are two or more electrical poles 4 to stimulate the gastric wall.

Once the electrocatheter is properly position, the stylet 8 is then again secured with forceps, and quick release connecting element 12 is cut easily and simply with endoscopic scissors as shown in FIG. 2. Preferably, the quick release connecting element 12 is cut as possible to the stylet. The stylet is then removed from the abdominal cavity of the patient. Using thread 30 attached to ring 19 on sheath 16 the electric terminal may be extracted from the abdomen for connecting to an appropriate power source or an electric stimulator, for instance, such as a pacemaker or electric recorder.

Once the electric terminal is outside the abdomen, small loop 18 is removed and sheath 16 is removed from electric terminal 5 in order to expose the electric terminal. The operation is thus performed in a dry arena, after surgical gloves have been changed. Electric terminal 5 is then connected to a pacemaker or a recorder, and the proper functioning of the system and the integrity of the electrocatheter are checked using the appropriate instrument. After gently pulling the electrocatheter toward the outside so as to reduce to a minimum length its presence in the abdomen, cursor 21 is slid towards the abdominal wall and is then secured to the electrocatheter using, for example, a nylon thread. The electrocatheter is then anchored via extension 23, by means of thread 25, to the abdominal wall, preferably to the muscular fascia, by a nylon suture. In this manner, the electrocatheter is secured in two positions: (1) around the tissue to be stimulated by tines 14 and 15 and (2) to the abdominal wall via extension 23.

Figure 3:
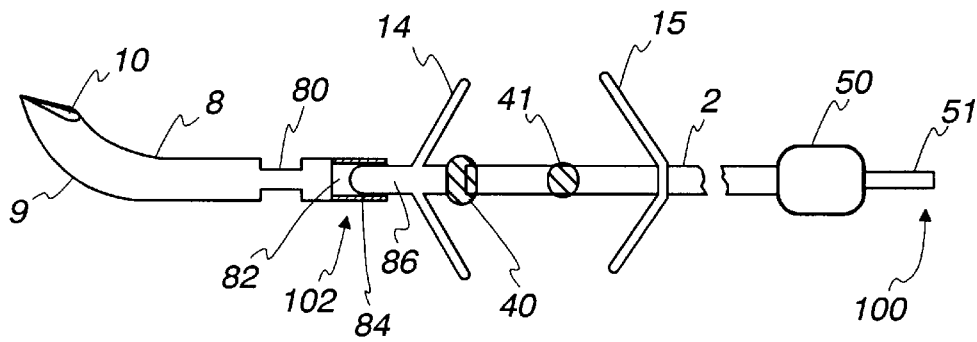
FIG. 3 is a schematic side view of a simplified embodiment of the implant device according to this invention.

A simplified embodiment of the present electrocatheter is shown in FIG. 3. In this embodiment, the stylet 8 is attached to the elongated body 2 at distal end 102. The stylet 8 in this embodiment is attached to the elongated body 2 using a flexible tube 84 (preferably medical-grade silicone similar to the insulating cover of the elongated body 2) that fits over the end 86 of elongated body 2 and the hub 82 of stylet 8. The connection may be strengthen, if desired, using medical-grade adhesive and/or a thin wire joining the stylet 8 and the elongated body 2. Of course, if such a wire is used to strengthen the connection, it should be non-conducting or electrically isolated from the electrical circuit used for stimulation. The elongated body 2 has two opposite set of tines or wings 14 and 15 with the appropriate poles 40 and 41 located there between. The elongated body 2 terminates in electrical terminal 5 having electrical poles 50 and 51 at proximal end 100. In operation, the electrocatheter is placed and positioned in the same manner as described above for the embodiment shown in FIGS. 1 and 2 except that the electrical terminal 5 remains outside the body cavity. Thus, once the electrocatheter has been correctly positioned within the body cavity, the electrical terminal 5 can be attached to the appropriate power source. Thus, the simplified electrocatheter shown in FIG. 3 does not require the movable cursor 21 or the sheath 16 to protect the electrical terminal 5 since the electrical terminal 5 remains outside the body cavity during the implantation procedure. Preferably the stylet 8 has one or more flattened portions 80 to help the surgeon grasp, manipulate, and guide the implant device to the proper position using forceps or other surgical instruments.

In operation, the electrocatheter shown in FIG. 3 is placed using essentially the same surgical procedure as described above. Once in place, the two poles 50 and 51 of electrical terminal 5 are attached to a power source. One pole 50 of the electrical terminal 5 is electrically connected to one pole 40 and the other pole 51 of the electrical terminal 5 is electrically connected to the other pole 41 through the elongated body. The electrical circuit is completed via the tissue to be stimulated and/or monitored. Thus, as those skilled in the art will understand, the overall electrical circuit within the implant device runs from one pole 50 of the electrical terminal 5 along a first electrical path through the elongated body 2 to electric pole 40, through the tissue to be stimulated to the other electric pole 41, and then from the other electric pole 41 through a second and separate electric path through the elongated body 2 to the other pole 51 in the electrical terminal 5. As those skilled in the art will also realize, the materials of construction and the methods of making the electrical circuit for the implant devices of this invention, including the poles 40, 41, 50, and 51 as well as the internal electrical connections, are well known in the art.

Figure 4A:
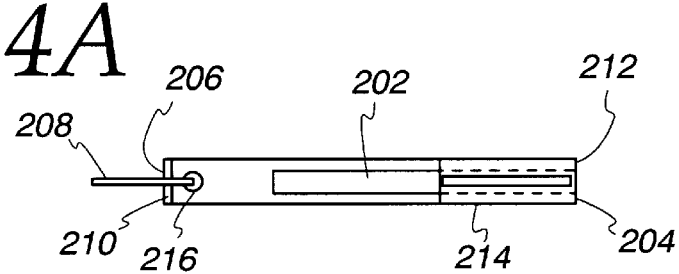
FIG. 4 illustrates one embodiment of the handle of the present invention wherein the handle has a fin adapted for grasping with laparoscopic forceps. Panel A is cross-sectional side view; panel B is a side view rotated 90 degrees from panel A; panel C is an end view of the proximal end of the handle.
Figure 4B:
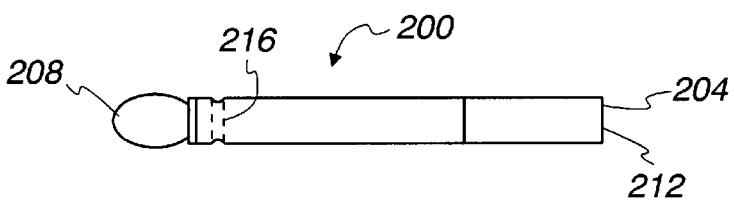
Figure 4C:
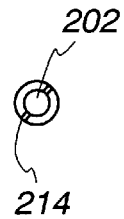
Figure 5A:
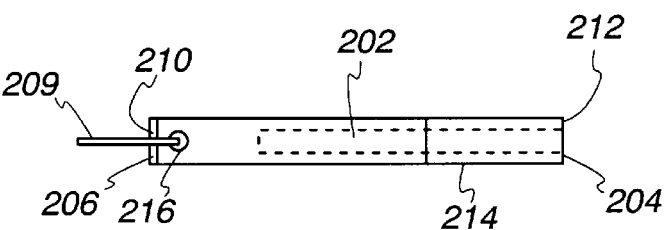
FIG. 5 illustrates another embodiment of the handle of the present invention wherein the handle has a loop adapted for grasping with laparoscopic forceps. Panel A is cross-sectional side view; panel B is a side view rotated 90 degrees from panel A; panel C is an end view of the proximal end of the handle.
Figure 5C:
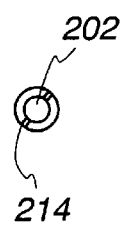
Figure 5B:
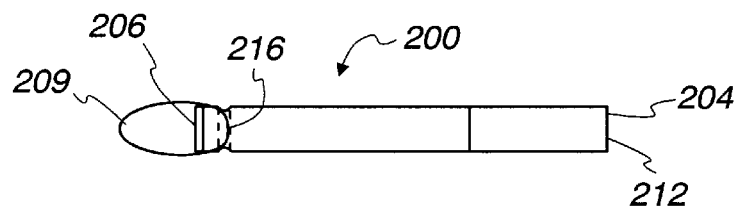
Figure 6:
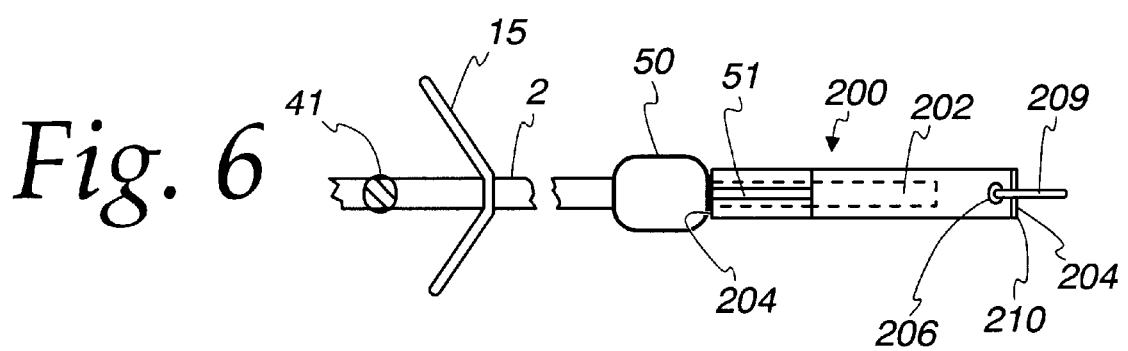
FIG. 6 illustrates the proximal end of an implant device (from FIG. 3) coupled with a handle according to the invention.

The handles of the present invention are shown in FIGS. 4–6. Preferably, the handles are both relatively thin and elongated. The handle 200 in FIGS. 4 and 5 has a distal end 204 and a proximal end 206. Attached to the proximal end 206 is grasping means such as a molded fin or tail 208 (FIG. 4) or a loop 209 (FIG. 5) which can easily be grasped using laparoscopic forceps. The distal end 204 has a inside bore or partial passageway 202 for receiving, and attaching to, the proximal end of the medical device (for example, the electrical pole 51 in FIG. 3). Thus, at least portion of the handle adjacent to the distal end 204 is hollow to receive the proximal end of the medical device. Any suitable attachment means for firmly attaching the handle 200 to the medical device can be used. For example, a friction fit, whereby the proximal end (e.g., the electrical pole 51 in FIG. 3) of the medical device is simply inserted into bore 202 can be used. A slot 214 (or multiple slots) can be provided in distal end 214 of handle 200 so that the proximal end 214 can be compressed (for example, by tightly winding surgical string, suture, or other flexible thread material around the proximal end 214) to more firmly grasp the proximal end of the medical device. The hollow portion can be different shapes (e.g., circular, square, oval, rectangular) depending on the shape of the proximal end of the particular medical device to be attached. Of course, other attachment means, including for example, internal bore threads with corresponding threads on the medical device, lure-type locks, lock and key-type devices, snap-type devices, and the like, can be used. It is generally preferred that the attachment means provide a secure attachment during manipulation but also allows for easy removal by the surgeon at the appropriate time. A especially preferred attachment means uses the slot 214 and a means for compressing the proximal end 202 tightly around the proximal end of the medical device (such compressing means include, for example, surgical string or suture which is tightly wrapped and tied around the handle to compress the proximal end 202 around the inserted portion of the medical device). The compression means can then be cut or otherwise removed when it is desired to remove the handle 200.

Preferably, the handle 200 is relatively thin and elongated to allow it, along with the attached medical device, to be more easily passed through the trocar in either direction. Even more preferably, the handle 200 has bevels or tapers 210 and/or 212 at the proximal end 206 and distal end 204, respectively, to allow the handle to pass more easily through the trocar; these beveled ends 210 and 212 also reduce the reduce the risk of leakage (i.e., help maintain an airtight seal) as the handle is passed through the trocar (i.e., either inserted or removed from the abdominal cavity). The degree of taper of the ends 204 and 206 can be varied as needed to help assist in maintaining an airtight seal during passage through the trocar. Generally, the outside diameter of the handle 200 is in the range of about 2 to 6 mm and the length (from ends 204 to 206) is in the range of about 1 to 3 inches. Preferably, the outside diameter of the handle 200 is approximately the same as the outside diameter of the elongated portion of the medical device to which the handle is attached to allow for easy passage of the medical device/handle combination through the trocar. Of course, the dimensions of the handle can be varied as needed for particular situations and/or medical devices.

The handle can be made of any suitable biocompatable material known in the art. Preferably, the handle is a relatively hard material such as, for example, silicone, PVC, or other plastic material so that the underlying device (i.e., the portion of the device contained in passageway 202) is not damaged when forceps are used to grasp the handle. If desired, especially where more than one medical device is to be used and/or implanted in a given operation, the handles can be color coded to help the surgeon identify the various instruments within the abdominal cavity. Likewise, the cross-sectional shape of passageway 202 could be varied so that only a given medical device could be attached to a given colored handle, thereby further helping the surgeon to easily identify specific devices or instruments during the surgical procedure.

The fin 210 and/or loop 209 are designed to be easily grasped by laparoscopic forceps. The fin 210 and/or loop 209 can be attached to the handle 200 in a number of ways. For example, the fin 210 and/or loop 209 can be molded integrally with the handle or pivotally attached to the handle 200 via hole 216. Generally, the fin 210 and/or loop 209 are constructed of biocompatable materials but are more flexible than the materials used to form the handle itself. By allowing the fin 208 and/or loop 209 to be pivotally mounted via hole 216, the handle is essentially self aligning; that is, grasping and pulling the handle using fin 208 and/or loop 209 orients the long dimension of handle 200 so that it can easily be pulled through the trocar. If desired, the fin 208 can have ridges or other raised dimensions on its surface (such as, for example, flattened portions such as cutouts 80 in stylet 8) to allow the forceps to obtain a better grip.

If desired, the handle may also contain a magnet (or a magnetic material) so that the handle (and the proximal end of the medical device), or the handle itself if it were become disengaged from the medical device, could be easily located using an appropriate tool with either a magnet or magnetic material attached to one end. Preferably such a magnet or magnetic material is sealed or otherwise contained within the handle (e.g., near the proximal end 206) so as to avoid direct contact with bodily fluids or tissue.

FIG. 6 illustrates the use of handle 200 with the preferred electrocatheter of FIG. 3. Only a portion of the preferred electrocatheter is shown. The electrical pole 51 of the electrocatheter is inserted into passageway 202 of the handle 200. Thus, the proximal end of the electrocatheter is coupled to the distal end 204 of the handle 200. The loop 209 now forms the proximal end of the electrocatheter/handle combination. Using laparoscopic forceps, the electrocatheter/handle combination can be manipulated and positioned for easy removal through the same trocar through which the forceps are inserted. The beveled or tapered end 210 allows the electrocatheter/handle combination to be easily removed through the trocar and reduces the risk of breaking the airtight seal. Once the junction of the electrocatheter and the handle is outside the abdomen, the surgeon can easily separate the electrocatheter and handle, thereby exposing the electrical connector 51. Although not shown, the handle could easily be modified so as to cover, if desired, the electrical pole 50 as well.

It has been proven in practice that the implant device, either alone or in conjunction with the handle described herein, according to the invention is particularly useful as stated above. The invention so described may be subject to numerous modifications and variations, all of which fall within the scope of the inventive concept; furthermore, all the details may be replaced by technically equivalent elements. In practice, the materials used, as well as the dimensions, may be varied according to need and the state of the art. Although this implant device and/or handle has been mainly described relative to its use in the gastrointestinal tube, it is primarily intended to be used in the endo-abdominal cavity including all viscera therein; such viscera include, but are limited to, tissues associated with the stomach, intestines, gall bladder, spleen, urinary tract, bladder, muscles, and the like. Moreover, although this implant device has been described in the context of use within the endo-abdominal cavity, it can, of course, be used in other portions of the body with appropriate modifications.

What is claimed is:

1. An implant device adapted for electrostimulation or electrical monitoring of tissue to be treated within the endo-abdominal cavity, said implant device comprising (1) an elongated body having a distal end and a proximal end, (2) a penetration mechanism at the distal end of the elongated body to penetrate the tissue to be treated, (3) a quick release connecting mechanism adjacent to the penetration mechanism, (4) a first and second sets of flexible tines adjacent and proximal to the quick release connecting mechanism to secure the implant device to the tissue to be treated wherein the first and second sets of tines are spaced apart along the elongated body a distance sufficient to span the tissue such that the first set of tines are located between the quick release connecting mechanism and the second set of tines, (5) at least two electric poles located between the two sets of flexible tines, (6) an electrical connection terminal at the proximal end of the elongated body for connection to a power source, and (7) a relatively hard, elongated handle having a proximal end and a distal end which can be attached to the proximal end of the elongated body;

wherein the two or more electric poles are electrically connected to electrical connection terminal; wherein the quick release connecting mechanism is effective to separate the penetration device from the elongated body once the implant device is properly positioned in the endo-abdominal cavity; wherein the distal end of the handle is adapted for attachment to the proximal end of the elongated body and the proximal end of the handle has grasping means whereby the handle can be grasped and manipulated using forceps; and wherein the handle can be easily separated from the proximal end of the elongated body at a desired time.

2. A device according to claim 1 wherein the handle also protects the electrical connection terminal from bodily fluids.

3. A device according to claim 1, wherein the penetration mechanism includes a stylet with one smooth curved non-cutting section with a cutting point and a cavity on the opposite end for attachment to the distal end of the elongated body.

4. A device according to claim 3, wherein the quick-release connecting mechanism includes a connecting element, one end of which is connected to distal end of the elongated body and the other end of which is lodged in the cavity on the stylet.

5. A device according to claim 1, wherein first set of tines are angled towards the proximal end of the elongated body such that they can pass easily through a tunnel in the tissue to be stimulated formed by the penetration mechanism and the second set of tines are angled towards the distal end of the elongated body such they resist passage through the tunnel.

6. A device according to claim 4, wherein first set of tines are angled towards the proximal end of the elongated body such that they can pass easily through a tunnel in the tissue to be stimulated formed by the penetration mechanism and the second set of tines are angled towards the distal end of the elongated body such they resist passage through the tunnel.

7. A device according to claim 1, wherein non-electrical conducting portions of the elongated body, except the penetration mechanism, which are inserted into the endo-abdominal cavity and are in direct contact with tissue therein are formed from medical-grade silicone.

8. A device according to claim 4, wherein non-electrical conducting portions of the elongated body, except the penetration mechanism, which are inserted into the endo-abdominal cavity and are in direct contact with tissue therein and the handle are formed from medical-grade silicone.

9. A device according to claim 3, wherein the stylet has a flattened portion to allow the stylet to be easily grasped and maneuvered with surgical instruments.

10. A device according to claim 4, wherein the stylet has a flattened portion to allow the stylet to be easily grasped and maneuvered with surgical instruments.

11. A device according to claim 8, wherein the stylet has a flattened portion to allow the stylet to be easily grasped and maneuvered with surgical instruments.

12. A device according to claim 1, wherein the handle has bevels at both its distal and proximal ends to allow the handle to more easily pass through a trocar.

13. A device according to claim 11, wherein the handle has bevels at both its distal and proximal ends to allow the handle to more easily pass through a trocar.

14. An implant device adapted for electrostimulation and electrical monitoring of tissue to be treated within a cavity of the human body, said implant device comprising (1) an elongated body having a distal end and a proximal end, (2) a penetration mechanism at the distal end of the elongated body to penetrate the tissue to be treated, (3) a quick release connecting mechanism adjacent to the penetration mechanism, (4) a first and second sets of flexible tines adjacent and proximal to the quick release connecting mechanism to secure the implant device to the tissue to be treated wherein the first and second sets of tines are spaced apart along the elongated body a distance sufficient to span the tissue such that the first set of tines are located between the quick release connecting mechanism and the second set of tines, (5) at least two electric poles located between the two sets of flexible tines, (6) an electrical connection terminal at the proximal end of the elongated body for connection to a power source, and (7) a relatively hard, elongated handle having a proximal end and a distal end which can be attached to the proximal end of the elongated body;

wherein the two or more electric poles are electrically connected to electrical connection terminal; wherein the quick release connecting mechanism is effective to separate the penetration device from the elongated body once the implant device is properly positioned in the body cavity; wherein the distal end of the handle is adapted for attachment to the proximal end of the elongated body and the proximal end of the handle has grasping means whereby the handle can be grasped and manipulated using forceps; and wherein the handle can be easily separated from the proximal end of the elongated body at a desired time.

* * * * *

UNITED STATES PATENT AND TRADEMARK OFFICE
CERTIFICATE OF CORRECTION

PATENT NO. : 6,041,258
DATED : March 21, 2000
INVENTOR(S) : Cigaina, et al.

It is certified that error appears in the above-indentified patent and that said Letters Patent is hereby corrected as shown below:

TITLE PAGE

Title should read -- MEDICAL STIMULATION AND MONITORING DEVICE WITH QUICK RELEASE MECHANISM AND DETACHABLE HANDLE FOR IMPLANTATION IN A BODY CAVITY --

Please insert on the Title Page:

-- [30] Foreign Application Priority Data
   May 28, 1997   [IT] Italy .............. MI97A001246 --

Signed and Sealed this

Twenty-seventh Day of February, 2001

Attest:

NICHOLAS P. GODICI

Attesting Officer   Acting Director of the United States Patent and Trademark Office